United States Patent [19]

Floyd, Jr. et al.

[11] Patent Number: 4,485,114

[45] Date of Patent: Nov. 27, 1984

[54] ARYLGLYOXALS USEFUL AS HYPOGLYCEMIC AGENTS

[75] Inventors: Middleton B. Floyd, Jr., Suffern, N.Y.; Vern G. DeVries, Ridgewood, N.J.

[73] Assignee: American Cyanamid Company, Stamford, Conn.

[21] Appl. No.: 459,450

[22] Filed: Jan. 20, 1983

[51] Int. Cl.³ ............... A61K 31/185; A61K 31/12; C07C 143/42; C07C 49/82
[52] U.S. Cl. .................... 424/315; 260/509; 260/511; 424/330; 424/331; 564/433; 568/42; 568/43; 568/331
[58] Field of Search ............... 260/511, 509; 564/431, 564/342, 169, 433; 568/337, 42, 43, 331; 424/315, 331, 330

[56] References Cited

PUBLICATIONS

Chem. Abstract, vol. 71, No. 13, 59322a, p. 257, 1969.
Chem. Abstract, vol. 84, No. 21, 150468g, pp. 532-533, 1976.

Primary Examiner—Nicky Chan
Attorney, Agent, or Firm—Edward A. Conroy, Jr.

[57] ABSTRACT

Arylglyoxals which are new compounds, which are active as hypoglycemic agents.

20 Claims, No Drawings

ARYLGLYOXALS USEFUL AS HYPOGLYCEMIC AGENTS

BACKGROUND OF THE INVENTION

This invention relates to arylglyoxals and various hydrates and adducts formed from them, which are new compounds useful as pharmaceutical agents. The novel compounds of this invention are hypoglycemic agents capable of ameliorating diabetes mellitus in mammals by acting to simulate and/or potentiate the action of insulin. This invention further relates to methods for treating diabetes mellitus in mammals in need of such treatment. In addition, this invention is concerned with pharmaceutical compositions for the utilization of these compounds in the treatment of diabetes mellitus. Further, this invention relates to the chemical synthesis of the compounds disclosed herein.

The disease diabetes mellitus is characterized by metabolic defects in the production and utilization of glucose which result in the failure to maintain appropriate blood sugar levels. The result of this defect is elevated blood glucose or hyperglycemia. Research on the treatment of diabetes has centered on attempts to normalize fasting and postprandial blood glucose levels. Treatments have included parenteral administration of exogenous insulin, oral administration of drugs, and dietary therapies.

Initially it was thought that hyperglycemia was simply the result of a deficiency in the supply of insulin, the principle hormone which controls glucose metabolism. As a result, research focused on the source of insulin production, the beta cells of the pancreas, and pharmaceutical agents were discovered which stimulated the production of insulin by the pancreas. Although it remains true that a deficiency of insulin does cause hyperglycemia it has now been recognized that other metabolic defects can be major cause of elevated blood glucose.

In Type I diabetes, also called juvenile onset or insulin-dependent diabetes, insulin deficiency is indeed the cause of hyperglycemia. However, the majority of diabetics suffer from a form of the disease referred to as Type II diabetes, also called maturity onset or non-insulin dependent diabetes. A main characteristic displayed by Type II diabetics is insulin resistance or insulin insensitivity. Insulin resistance is a condition in which available insulin, secreted by the pancreas and circulating in the blood stream, fails to stimulate sufficient glucose uptake and utilization in insulin-sensitive tissue. This inability of certain tissues including liver, muscle, and fat, whose metabolic machinery is normally sensitive to insulin, to utilize glucose efficiently or to control endogenous glucose synthesis and glycogenolysis, results in elevated blood glucose.

Compounds which simulate and/or potentiate the biological action of insulin would be beneficial in the treatment of hyperglycemia resulting from mild to moderate insulin insufficiency or insulin insensitivity. A compound which would simulate or mimic insulin's action would correct both insulin deficiency and insulin resistance by its own insulin-like action. Further, a compound which would potentiate insulin's action would ameliorate insulin deficiency by rendering the small amount of insulin which is present more efficacious and would decrease insulin resistance directly by acting synergistically to make insulin more effective. Thus compounds which show insulin-like and/or insulin potentiating activity would be beneficial for the treatment of hyperglycemia occuring either in Type I or Type II diabetes.

The compounds of the present invention simulate and potentiate the biological action of insulin. They simulate insulin's action at least in part by promoting the cellular uptake and metabolism of glucose in the absence of insulin. They potentiate insulin's action by exerting a synergistic effect on insulin action in the presence of sub-maximal concentrations of insulin. The exact mechanism by which the compounds of this invention act to produce these effects is not known and the invention should not be construed as limited to any particular mechanism of action. Nonetheless, the compounds of this invention are useful for the treatment of hyperglycemia and diabetes in mammals.

SUMMARY OF THE INVENTION

This invention relates to new aryglyoxals and their addition products, their use in the treatment of diabetes mellitus, pharmaceutical compositions containing them and their chemical synthesis. More particularly, it is concerned with compounds which may be represented by formula I:

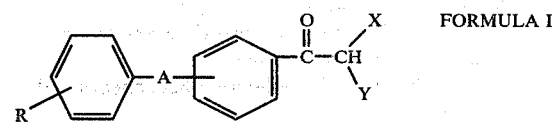

FORMULA I wherein A is selected from the group consisting of oxygen, sulfur, imino and ($C_1$-$C_4$) alkyl imino; R represents at least one substituent, selected from the group consisting of ($C_1$-$C_4$) alkyl thio, hydrogen, trifluoromethyl and halogen, with the proviso that when A is oxygen or sulfur, R cannot be hydrogen or halogen; X and Y may be the same or different and are independently selected from the group consisting of hydroxy, ($C_1$-$C_4$) alkoxy, anilino, carboxyanilino, ($C_1$-$C_4$) carboalkoxy anilino and $SO_3Q$; with the further proviso that X and Y taken together may represent oxygen; Q is an alkali metal or alkaline earth metal; and the hydrates thereof.

In more preferred embodiments, this invention is concerned with compounds which may be represented by formula I, wherein A is selected from the group consisting of oxygen, sulfur, imino and methylimino; R represents at least one substituent selected from the group consisting of methylthio, hydrogen, trifluoromethyl and chloro, with the proviso that when A is oxygen or sulfur, R cannot be hydrogen or chloro; X and Y may be the same or different and are independently selected from the group consisting of hydroxy, ethoxy, carboxyanilino and —$SO_3Na$; with the further proviso that X and Y taken together may represent oxygen; and the hydrates thereof.

The more preferred embodiments of this invention are concerned with the following specific compounds:
hydroxy[p-(α,α,α-trifluoro-m-tolyloxy)benzoyl]methanesulfonic acid, sodium salt, hemihydrate
α-oxo-4-[3-(trifluoromethyl)phenoxy]benzeneethanal, hemihydrate
(p-anilinobenzoyl)hydroxy-methanesulfonic acid, sodium salt
p-[[α-hydroxy-p-(α,α,α-trifluoro-m-tolyloxy)phenacyl]amino]benzoic acid 4-[[1-ethoxy-2-oxo-2-[4-[3-(trifluoromethyl)phenoxy]-phenyl]ethyl]amino]benzoic acid α-hydroxy-β-oxo-4-[[3-(trifluoromethyl)phenyl]thio]-benzeneethanesulfonic acid, sodium salt α-hydroxy-β-oxo-4-[4-(trifluoromethyl)phenoxy]benzeneethanesulfonic acid, sodium salt, hemihydrate 2,2-hydroxy-1-[4-[4-(trifluoromethyl)phenoxy]phenyl]ethanone 2,2-hydroxy-1-[4-[4-(methylthio)phenoxy]phenyl]ethanone 2,2-hydroxy-1-[4-[[3-(trifluoromethyl)phenyl]thio]phenyl]ethanone α-hydroxy-β-oxo-4-[[3-(trifluoromethyl)phenyl]amino]benzeneethanesulfonic acid, sodium salt 4-[(3-chlorophenyl)amino]-α-hydroxy-β-oxo-benzeneethanesulfonic acid, sodium salt α-hydroxy-β-oxo-3-[3-(trifluoromethyl)phenoxy]benzeneethanesulfonic acid, sodium salt α-hydroxy-β-oxo-4-[3,5-bis(trifluoromethyl)phenoxy]-benzeneethanesulfonic acid, sodium salt 2,2-dihydroxy-1-[4-(phenylamino)phenyl]ethanone α-hydroxy-β-oxo-4-[[4-(trifluoromethyl)phenyl]amino]benzeneethanesulfonic acid, sodium salt α-hydroxy-4-[(3-methylphenyl)amino]-β-oxo-benzeneethanesulfonic acid, sodium salt α-hydroxy-4-(methylphenylamino)-β-oxo-benzeneethanesulfonic acid, sodium salt α-oxo-4-[3-(trifluoromethyl)phenoxy]benzeneethanal, monohydrate This invention is further concerned with a method of treating diabetes mellitus in a mammal in need of such treatment which comprises administering to said mammal an effective amount of a compound as recited above.

This invention also relates to a method of treating hyperglycemia in a mammal in need of such treatment which comprises administering to said mammal an effective amount of a compound as recited above.

This invention also relates to a pharmaceutical composition which comprises an effective antidiabetic amount of a compound as recited above in association with a pharmaceutically acceptable carrier.

This invention also relates to a pharmaceutical composition which comprises an effective hypoglycemic amount of a compound as recited above in association with a pharmaceutically acceptable carrier.

Finally, this invention relates to processes for preparing compounds as recited above.

DETAILED DESCRIPTION OF THE INVENTION

Certain of the compounds of this invention may be prepared according to the following reaction sequence:

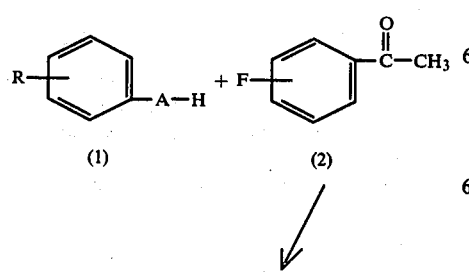

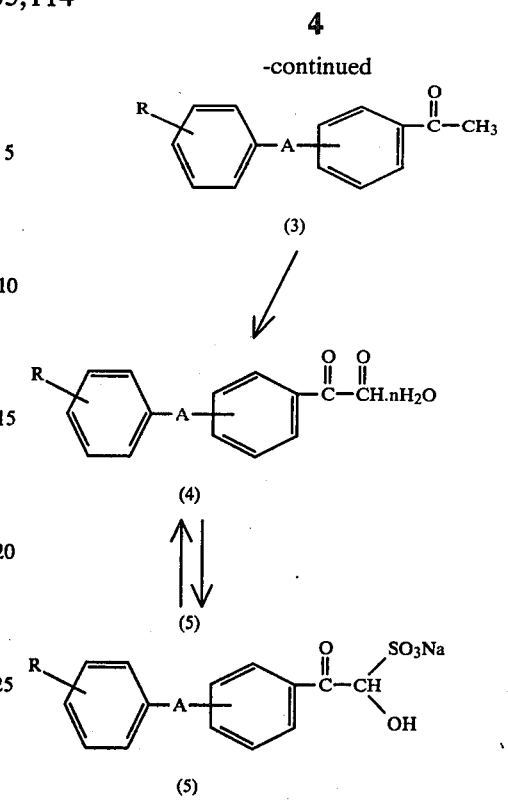

In accordance with the above reaction sequence, a phenol or thiophenol (1) where R is as described above and A is oxygen or sulfur is combined with a fluoroacetophenone (2) and treated with potassium carbonate in dimethylacetamide under an inert atmosphere at reflux for 8–48 hours, then cooled, poured into ice and extracted with ether. The extract is evaporated and distilled, giving the acetophenone (3) where R is as described above and A is oxygen or sulfur. The acetophenone (3) is then dissolved in dimethylsulfoxide and treated with aqueous hydrobromic acid at 45°-65° C. for 18-48 hours, poured into ice and extracted with ethyl acetate. The extract containing (4) where n may vary from almost zero to one or more, is concentrated, dissolved in a mixture of ethanol and water at 50°-70° C. and treated with sodium metabisulfite at the boiling point for 5 minutes, then cooled under argon at 0° C., giving (5), where R and A are as described above. The sodium bisulfite derivative (5) is then suspended in water at 40°-60° C., acidified, heated at 90°-100° C. for 1-2 hours, cooled and extracted with ether. The ether extract is concentrated giving (4) where R and A are as described above and A is O or S. Compounds of structure (4) are obtained in various degrees of hydration; that is, n may vary from almost zero to one or more.

Alternatively, the acetophenone (3), where R and A are as described above, is treated with selenium dioxide in aqueous dioxane at reflux, under an inert atmosphere for 12-24 hours. The reaction mixture is then filtered and the filtrate evaporated, giving (4) where R is as decribed above, which may be converted to the methanesulfonic acid, sodium salt derivative (5) by treatment with sodium metabisulfite in aqueous ethanol.

To produce the compounds of formula I where R is as described above and A is —NH— or

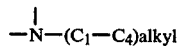

an appropriate substituted diphenylamine (6),

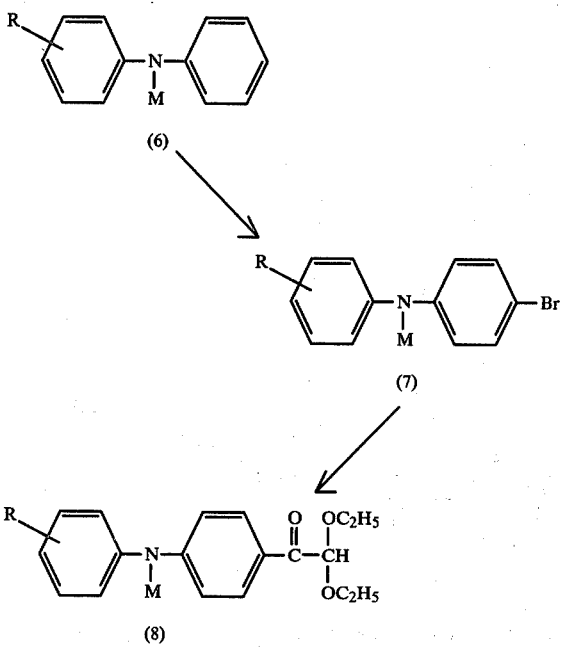

where R is as described above and M is hydrogen or $(C_1-C_4)$alkyl is treated with aqueous hydrobromic acid in dimethylsulfoxide for 4–10 hours, then poured into a mixture of ice and hydrochloric acid and extracted with methylene chloride. The extracts are concentrated to yield (7), which is then dissolved in ether or tetrahydrofuran in an inert atmosphere at $-78°$ to $-20°$ and treated with n-butyl lithium for 1–24 hours at $-78°$ to 25°. The lithium reagent thus obtained is treated with 1-(diethoxyacetyl)piperidine. This mixture is quenched with acetic acid in ether solution. The ether layer is separated, evaporated and purified by chromatography, giving (8), where R and M are as described above. This diethoxy derivative is then converted to (4) by treatment with aqueous hydrochloric acid in dioxane followed by basification in ether giving (4) where R is as described above and A is —NH— or

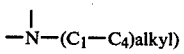

and after treatment with sodium bisulfite as described above, compound (5).

The compounds of this invention were tested for their insulin-like and insulin-potentiating activity according to the following procedure:

Male, Wistar strain, Royal Hart rats weighing 125–170 g. were sacrificed by decapitation. Their abdominal cavities were opened and distal or thin portions of epididymal fat pads excised, accumulated, and placed in 0.9% saline. The tissue was weighed and placed at a density of about 0.4 g./ml. in Krebs-Henseleit bicarbonate (KHB) buffer containing 5 mg. of crude bacterial collagenase per ml. [The KHB is composed of 118 mM sodium chloride; 4.7 mM potassium chloride; 1.2 mM calcium chloride; 1.2 mM potassium dihydrogen phosphate; 1.2 mM magnesium sulfate heptahydrate; 25 mM sodium bicarbonate and 0.3 mM glucose and is saturated with oxygen:carbon dioxide (95:5).] The tissues were incubated with collagenase for one hour at 37° C. with gentle agitation in a Dubnoff metabolic shaker. At the end of this digestion period the cells were washed five times with twice their volume of KHB buffer containing fatty acid free bovine serum albumin (Pentex Fraction V) at a concentration of 3%. The digest was filtered through two layers of gauze and suspended in KHB buffer with albumin to a volume ten times the initial total weight of the fat pads. Incubation of one ml. aliquots of the cell suspension was carried out in 17×100 mm plastic Falcon tubes. Cells were incubated in the presence or absence of test compound and insulin. All tubes contained 0.15 μCi D-glucose-U-$^{14}$C (specific activity >200 mC/mmole).

Recrystallized porcine insulin (specific activity=25.5 U/mg.) was dissolved in 0.9% saline adjusted to pH 3 with hydrochloric acid. The insulin was added to the cells at a concentration of approximately 5 U/ml. and control or basal cells received comparable volumes of pH 3 saline. Test compounds were dissolved in 50% dimethylsulfoxide-50% ethanol and added to the cells at a concentration of 100 μg/ml. Control cells received comparable volumes of dimethyl sulfoxide-ethanol.

After the tubes were loaded with insulin and test compound, or other vehicles, and cell suspension, they were capped with sleeve stoppers fitted with hanging, plastic center wells. Each well contained a small section of folded filter paper. The tubes were then gassed for about one minute with oxygen:carbon dioxide (95:5) via needles inserted through the septum of the stopper. Immediately after gassing, the radioactive glucose was injected into the incubate and the tubes were placed in a 37° C. metabolic shaking water bath and were incubated for one hour with agitation.

At the end of the incubation, 0.4 ml. of Hyamine hydroxide and then 0.5 ml. of 5N sulfuric acid were carefully injected into the center well and cell suspension, respectively. The acidified cell suspension was then incubated an additional 30 minutes at room temperature with gentle agitation. At the end of this carbon dioxide collection period, the center wells were dropped into vials containing 10 ml. of Dimiscint® scintillation cocktail and the radioactivity counted by liquid scintillation spectrometry.

The measurement of carbon dioxide radioactivity in counts per minute produced by these cells in the absence of both test compound and insulin is the basal level (b). Radioactivity produced in the presence of test compounds only, insulin only and both test compound and insulin are (c), (i) and (ci), respectively. Each of (c), (i) and (ci) is then expressed as a percent of the basal value:

$$C = \frac{c}{b} \; ; I = \frac{i}{b} \; ; CI = \frac{ci}{b} \; .$$

Finally, insulin-like activity (%C/I) is calculated using the formula $$\% \, C/I = \frac{(100)(C - 100)}{(I - 100)} \; ;$$

and insulin-potentiating activity (%P) is calculated using the formula $$\% P = \frac{(100)(CI - C - I + 100)}{(I - 100)}.$$

The results of this test on representative compounds of this invention appear in Table I.

TABLE I

| Compound | % C/I | % P |
|---|---|---|
| hydroxy[p-(α,α,α-trifluoro-m-tolyloxy)benzoyl]-methanesulfonic acid, sodium salt, hemihydrate | 404 | 222 |
| α-oxo-4-[3-(trifluoromethyl)phenoxy]benzene-ethanal, hemihydrate | 1229 | 205 |
| (p-anilinobenzoyl)hydroxy-methanesulfonic acid, sodium salt | 323 | 147 |
| p-[[α-hydroxy-p-(α,α,α-trifluoro-m-tolyloxy)-phenacyl]amino]benzoic acid | 435 | 753 |
| 4-[[1-ethoxy-2-oxo-2-[4-[3-(trifluoromethyl)-phenoxy]phenyl]ethyl]amino]benzoic acid | 270 | 71 |
| α-hydroxy-β-oxo-4-[[3-(trifluoromethyl)phenyl]-thio]benzeneethanesulfonic acid, sodium salt | 195 | 275 |
| α-hydroxy-β-oxo-4-[4-(trifluoromethyl)phenoxy]-benzeneethanesulfonic acid, sodium salt, hemihydrate | 108 | 205 |
| 2,2-hydroxy-1-[4-[4-(trifluoromethyl)phenoxy]-phenyl]ethanone | 377 | 95 |
| 2,2-hydroxy-1-[4-[4-(methylthio)phenoxy]-phenyl]ethanone | 257 | 77 |
| 2,2 hydroxy-1-[4-[[3-(trifluoromethyl)phenyl]-thio]phenyl]ethanone | 816 | 0 |
| α-hydroxy-β-oxo-4-[[3-(trifluoromethyl)phenyl]-amino]benzeneethanesulfonic acid, sodium salt | 515 | 136 |
| 4-[(3-chlorophenyl)amino]-α-hydroxy-β-oxo-benzeneethanesulfonic acid, sodium salt | 370 | 165 |
| α-hydroxy-β-oxo-3-[3-(trifluoromethyl)phenoxy]-benzeneethanesulfonic acid, sodium salt | 124 | 187 |
| α-hydroxy-β-oxo-4-[3,5-bis(trifluoromethyl)-phenoxy]benzeneethanesulfonic acid, sodium salt | 222 | 277 |
| 2,2-dihydroxy-1-[4-(phenylamino)phenyl]ethanone | 267 | 0 |
| α-hydroxy-β-oxo-4-[[4-(trifluoromethyl)phenyl]-amino]benzeneethanesulfonic acid, sodium salt | 158 | 0 |
| α-hydroxy-4-[(3-methylphenyl)amino]-β-oxo-benzeneethanesulfonic acid, sodium salt | 507 | 228 |
| α-hydroxy-4-(methylphenylamino)-β-oxo-benzene-ethanesulfonic acid, sodium salt | 162 | 105 |
| α-oxo-4-[3-(trifluoromethyl)phenoxy]benzene-ethanal, monohydrate | | |

When the compounds are employed for the above utility, they may be combined with one or more pharmaceutically acceptable carriers, e.g., solvents, diluents and the like, and may be administered orally in such forms as tablets, capsules, dispersible powders, granules, or suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 5 milligrams to about 100 milligrams per kilogram of animal body weight, preferably given in divided doses two to four times a day, or in sustained release form. For most large mammals, the total daily dosage is from about 500 milligrams to about 5,000 milligrams preferably from about 350 milligrams to 3,500 milligrams. Dosage forms suitable for internal use comprise from about 25 to 500 milligrams of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

4'-[3-(Trifluoromethyl)phenoxy]acetophenone

A stirred mixture of 90.6 g of 3-(trifluoromethyl)-phenol, 55.2 g of 4-fluoroacetophenone and 400 ml of dry dimethylacetamide was treated under argon with 71.9 g of anhydrous potassium carbonate in portions. The mixture was stirred and refluxed at 155°–160° C. on an oil bath for 18 hours. The mixture was cooled, poured into 1.5 Kg of ice and extracted with three portions of ether. The extracts were combined, washed successively with water, three 100 ml. portions of cold 1N sodium hydroxide, water and then brine, dried and evaporated to an oil. This oil was distilled at 105°–120° C., 0.15–0.20 mm Hg, giving the desired intermediate as an oil, bp 130°–142° C. (0.2 mm).

Using other phenol and thiophenol derivatives in the procedure of Example 1, the intermediates of Examples 2–5 (Table II) were obtained.

TABLE II

| Example | Intermediate | Physical Constant |
|---|---|---|
| 2 | 4'-[3-(Trifluoromethyl)phenylthio]-acetophenone | bp 110–115° C. (0.12 mm Hg) |
| 3 | 4-[4-(trifluoromethyl)phenoxy]-acetophenone | bp 100–110° C. (0.08 mm Hg) |
| 4 | 4-[4-(methylthio)phenoxy]-acetophenone | mp 83–84° C. |
| 5 | 4-[3,5-bis(trifluoromethyl)-phenoxy]acetophenone | bp 80–90° C. (0.06 mm Hg) |

EXAMPLE 6

Hydroxy[p-(α,α,α-trifluoro-m-tolyloxy)benzoyl]methanesulfonic acid, sodium salt

To a stirred solution of 353 g. of 4'-[3-trifluoromethyl)phenoxy]acetophenone in 2150 ml of dimethyl sulfoxide was added 430 ml of 48% aqueous hydrobromic acid during 15 minutes. The solution was stirred at 55° C. for 24 hours, then poured into 6 Kg of ice and extracted with four 1000 ml portions of ethyl acetate. The extracts were combined, washed successively with water, saturated sodium bicarbonate and brine, dried and concentrated in vacuo to an oil. This oil was dissolved in 2520 ml of ethanol and 840 ml of water at 60° C. with stirring and treated with 133 g. of sodium metabisulfite. The mixture was stirred at the boiling point for 5 minutes and then cooled under argon to 0° C. The resulting solid was collected, washed with ethanol and ether and dried, giving the desired product as a white solid, m.p. 190°–210° C. (dec.).

EXAMPLE 7

α-Oxo-4-[3-(trifluoromethyl)phenoxy]benzeneethanal, monohydrate

A 374 g. portion of hydroxy[p-(α,α,α-trifluoro-m-tolyloxy)benzoyl]methanesulfonic acid, sodium salt was suspended in 3485 ml. of water and the mixture was stirred at 50° C. while 316 ml. of 6N hydrochloric acid were added during 30 minutes. The cloudy solution was warmed slowly until sulfur dioxide evolution ceased and an oil began to separate at about 75° C., then was stirred and heated at reflux for 1.5 hours. The mixture was cooled and extracted with three 1000 ml. portions of ether. The extracts were combined, washed with water, saturated sodium bicarbonate and brine, dried and concentrated to a yellow solid. This solid was recrystallized from ether:hexane (1:1) at 5° C., to yield the desired product as a white solid, m.p. 73°–80° C.

EXAMPLE 8

α-Oxo-4-[3-(trifluoromethyl)phenoxy]benzeneethanal, hemihydrate

A 75 g. portion of α-oxo-4-[3-(trifluoromethyl)-phenoxy]benzeneethanl, monohydrate was dissolved in 700 ml. of boiling ether. The solution was diluted with 700 ml. of hexane and then concentrated to a volume of about 1000 ml. by boiling. This solution was cooled to approximately 5° and filtered to yield the desired product as a white solid, m.p. 78°–86° C.

EXAMPLE 9

α-Hydroxy-α-oxo-4-[[3-(trifluoromethyl)phenyl]thio]-benzeneethanesulfonic acid, sodium salt A mixture of 14.8 g. of 4'-[3-(trifluoromethyl)phenylthio]acetophenone, 5.83 g. of selenium dioxide, 3 ml. of water and 50 ml. of dioxane was refluxed under argon for 18 hours. The reaction was filtered through hydrous magnesium silicate and evaporated to an oil, which was the glyoxal hydrate corresponding to the title compound.

A 19.74 g. portion of this oil was dissolved in 50 ml. of ethanol and treated with 50 ml. of saturated aqueous sodium bisulfite. A 25 ml. portion of ethanol was added, the mixture was stirred overnight and the solid recovered by filtration. This solid was boiled in water, cooled and filtered, giving the desired product as a white crystalline solid, m.p. 170° C. (dec.).

Reaction of the intermediates of Examples 1–5 by the procedures of Example 6, 7, 8, or 9 gave the products of Examples 10–15 (Table III).

TABLE III

| Example | Intermediate of Example | Product | Physical Constant |
|---|---|---|---|
| 10 | 3 | α-hydroxy-β-oxo-4-[4-(trifluoromethyl)-phenoxy]benzeneethane-sulfonic acid, sodium salt | mp 210° (dec.) |
| 11 | 3 | 2,2-dihydroxy-1-[4-[4-(trifluoromethyl)-phenoxy]phenyl]ethanone | mp 78–84° C. |
| 12 | 4 | 2,2-dihydroxy-1-[4-[4-(methylthio)-phenoxy]phenyl]ethanone | mp 103–113° C. |
| 13 | 2 | 2,2-dihydroxy-1-[4-8 [3-(trifluoromethyl)phenyl]thio]phenyl]ethanone | mp 86–93° C. |
| 14 | 5 | α-hydroxy-β-oxo-4-[3,5-bis(trifluoromethyl)phenoxy]benzeneethane-sulfonic acid, sodium salt | |
| 15 | 1 | α-oxo-4-[3-(trifluoromethyl) phenoxy]benzeneethanal, hydrate | |

EXAMPLE 16

2,2-Diethoxy-1-[4-(phenylamino)phenyl]ethanone

A 33.8 g portion of diphenylamine was treated with a 20% solution of hydrobromic acid in dimethylsulfoxide (46 ml of 48% hydrobromic acid in 300 ml of dimethylsulfoxide) with rapid stirring for 7 hours. The solution was then poured into a mixture of 200 g of ice and 16 ml of 5N sodium hydroxide and then extracted into methylene chloride. The extract was washed with water, dried and evaporated to a solid, then recrystallized from petroleum ether, giving p-bromodiphenylamine.

A 2.48 g portion of p-bromodiphenylamine was stirred in 10 ml of ether under argon at −20° C., while 5.7 ml fo 2.1M n-butyllithium in hexane was added via a syringe over 5 minutes. The mixture was stirred for 24 hours with the addition of 5.7 ml of 2.1M n-butyllithium in hexane at 22 hours. The mixture was cooled in an ice bath and treated over 5 minutes at 0°–10° C. with a solution of 1-(diethoxyacetyl)piperidine in 10 ml of ether. The mixture was then stirred at room temperature followed by refluxing for 4 hours, then poured into a mixture of one ml of acetic acid in ether and ice. The ether layer was separated, washed with 1% aqueous acetic acid until the wash was acidic, then with water, saturated aqueous sodium bicarbonate and brine, dried and evaporated to a solid. This crude solid was dissolved in 15 ml of hexane plus a few drops of ethyl acetate and developed on a column. Fractions were eluted with hexane and then with 2:1 hexane:ethyl acetate, the latter yielding the desired intermediate.

Reaction of other substituted diphenylamines or N-methyldiphenylamines using the procedure of Example 16, gave the intermediates of Examples 17–20 (Table IV).

TABLE IV

| Example | Intermediate | Physical Constant |
|---|---|---|
| 17 | 2,2-diethoxy-1-[4-[(3-chlorophenyl)amino]phenyl]ethanone | oil |
| 18 | 2,2-diethoxy-1-[4-[[4-(trifluoromethyl)phenyl]amino]phenyl]ethanone | mp 110–115° C. |
| 19 | 2,2-diethoxy-1-[4-[(3-tolyl)amino]phenyl]ethanone | |
| 20 | 2,2-diethoxy-1-[4-[N—phenyl-N—methylamino]phenyl]ethanone | |

EXAMPLE 21

(p-Anilinobenzoyl)hydroxy-methanesulfonic acid, sodium salt

A stirred mixture of 2.10 g of 2,2-diethoxy-1-[4-(phenylamino)phenyl]ethanone in 70 ml of 0.7N hydrochloric acid and 70 ml of dioxane was refluxed for 3 hours, then cooled and the dioxane removed in vacuo. Ether was added with stirring and the pH adjusted to 8 with 5N sodium hydroxide. The ether extract was separated, washed with water and brine, dried and evaporated to a red gum which is the glyoxal hydrate corresponding to the title compound.

A 1.4 g portion of this gum was dissolved in 30 ml of hot ethanol and then treated with a solution of 1.08 g of sodium bisulfite in 10 ml of water. This solution was refluxed for 15 minutes, filtered while hot and the filtrate evaporated to a residue. The residue was crystallized from ether, then slurried in water, giving the desired product as a yellow solid, mp 170°–185° C. (dec.).

Reaction of the intermediates of Examples 16–20 by the procedure of Example 21, gave the products of Examples 22–25 (Table V).

TABLE V

| Example | Intermediate of Example | Product | Physical Constant |
|---|---|---|---|
| 22 | 17 | 4-[(3-chlorophenyl)amino]-α-hydroxy-β-oxo-benzeneethanesulfonic acid, sodium salt | mp 185–200° C. (dec.) |
| 23 | 16 | 2,2-dihydroxy-1-[4-(phenylamino)phenyl[ethanone | foam |
| 24 | 18 | α-hydroxy-β-oxo-4-[[4-(trifluoromethyl)-phenyl]amino]benzeneethanesulfonic acid, sodium salt | mp 180–195° C. (dec.) |
| 25 | 19 | α-hydroxy-4-[(3-methylphenyl)amino]-β-oxo-benzeneethanesulfonic acid, sodium salt | mp 170–190° C. (dec.) |
| 26 | 20 | α-hydroxy-4-(N—phenyl-N—methylamino)-β-oxo-benzeneethanesulfonic acid, sodium salt | mp 120–145° C. (dec.) |

EXAMPLE 27 p-[[α-Hydroxy-p-(α,α,α-trifluoro-m-tolyloxy)-phenacyl]amino]benzoic acid

A mixture of 5.62 g of 2,2-dihydroxy-4'-(α,α,α-trifluoro-m-tolyloxy)acetophenone, 2.06 g of p-aminobenzoic acid, 56 ml of tetrahydrofuran and 19 ml of water was stirred at reflux for 45 minutes, then cooled and the tetrahydrofuran evaporated. The oily residue was extracted with ether. The extract was washed with brine, dried and evaporated to a foam. This foam was stirred vigorously in 500 ml of hexane:ether (10:1), filtered, washed with the same solvent mixture and dried. This solid was mixed with 50 ml of ether, cooled to 0° C. and filtered. The filtrate was stirred and treated with petroleum ether until cloudy, then cooled and the product collected, giving the desired product as a light yellow solid, mp 120°–140° C.

EXAMPLE 28

4-[[1-Ethoxy-2-oxo-2-[4-[3-(trifluoromethyl)phenoxy]-phenyl]ethyl]amino]benzoic acid A mixture of 5.62 g of 2,2-dihydroxy-4'-(α,α,α-trifluoro-m-tolyloxy)acetophenone, 2.47 g of p-aminobenzoic acid and 100 ml of ethanol was refluxed for 30 minutes and then 50 ml of toluene were added. The mixture was evaporated to dryness and the refluxing with ethanol and toluene repeated twice. Then the ethanol was evaporated giving a residue which was dissolved in 150 ml of ether, 75 ml of petroleum ether was added and the mixture cooled to 0° C., giving the desired product as an off-white powder, mp 109°–122° C. (dec.).

EXAMPLE 29

α-Hydroxy-β-oxo-4-[[3-(trifluoromethyl)phenyl]amino]benzeneethanesulfonic acid, sodium salt A mixture of 13.0 g of m-trifluoromethylphenyl bromide, 8.68 g of p-acetylaminoacetophenone, 14.5 g of potassium carbonate, 0.45 g of copper powder and 40 ml of decahydronaphthalene was stirred at reflux on an oil bath at 200° C., under argon for 64 hours. The mixture was then cooled, stirred with 200 ml of acetone, filtered and the filtrate evaporated to a semi-solid. Evaporative distillation gave a semi-solid which was dissolved in 150 ml of ethanol and 150 ml of concentrated hydrochloric acid and refluxed under argon for 30 minutes. The mixture was cooled, partially evaporated and partitioned between 50% saturated brine and ethyl acetate. The ethyl acetate layer was washed with water and brine, dried and evaporated to a semi-solid. This semi-solid was purified by chromatography, giving 4'-[3-(trifluoromethyl)phenylamino]acetophenone which was then converted to the desired product by the procedure of Example 9, giving the product as a light amber solid, m.p. 180°–195° C. (dec.).

EXAMPLE 30

α-Hydroxy-β-oxo-3-[3-(trifluoromethyl)phenoxy]benzeneethanesulfonic acid, sodium salt To a stirred solution of 3.10 g of methyl methyl thiomethylsulfoxide in 20 ml of tetrahydrofuran under argon in an ice bath was added 10.4 ml. of 2.4M n-butyllithium in hexane via a syringe during 15 minutes, maintaining the temperature at 10°–15° C. The mixture was stirred at 10° C. for 10 minutes, then recooled and a solution of 5.32 g of m-[m-(trifluoromethyl)phenoxy]-benzaldehyde in 10 ml of tetrahydrofuran was added during 10 minutes, maintaining the temperature at <10° C. The resulting solution was stirred at 0°–5° C. for one hour, then the tetrahydrofuran was evaporated. The resulting yellow foam was added to dimethyl sulfoxide and cooled in an ice bath while aqueous hydrobromic acid was added. The reaction was then heated at 50° C. overnight, then poured into ice and extracted with ethyl acetate. The extract was washed with water, saturated sodium bicarbonate and brine, dried and evaporated, giving 2,2-dihydroxy-3'-(α,α,α-trifluoro-m-tolyloxy)acetophenone as a yellow oil.

The above oil, 1.2 g of sodium bisulfite, 54 ml of ethanol and 18 ml of water were combined, heated on a steam bath for 10 minutes, then stirred at room temperature overnight. The solvent was evaporated and the residue stirred vigorously with acetone and the resulting solid collected. This solid was stirred vigorously with ethyl acetate, warmed and the solid collected, giving the desired product as a white solid.

We claim:

1. A compound selected from the group consisting of those of the formula:

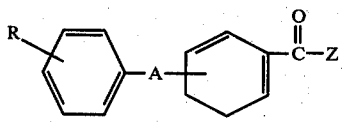

wherein A is selected from the group consisting of oxygen, sulfur, imino and $(C_1-C_4)$alkylimino; R represents at least one substituent selected from the group consisting of $(C_1-C_4)$alkylthio, hydrogen, trifluoromethyl and halogen with the proviso that when A is oxygen or sulfur then R cannot be hydrogen or halogen; Z is a moiety of the formulae:

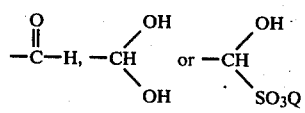

wherein Q is an alkali metal or alkaline earth metal; and the hydrates thereof.

2. The compound according to claim 1; hydroxy[p-(α,α,α-trifluoro-m-tolyloxy)benzoyl]methanesulfonic acid, sodium salt, hemihydrate.

3. The compound according to claim 1; α-oxo-4-[3-(trifluoromethyl)phenoxy]benzeneethanal, hemihydrate.

4. The compound according to claim 1; (p-anilinobenzoyl)hydroxy-methanesulfonic acid, sodium salt.

5. The compound according to claim 1; α-hydroxy-β-oxo-4-[[3-(trifluoromethyl)phenyl]thio]benzeneethanesulfonic acid, sodium salt.

6. The compound according to claim 1; α-hydroxy-β-oxo-4-[4-(trifluoromethyl)phenoxy]benzeneethanesulfonic acid, sodium salt, hemihydrate.

7. The compound according to claim 1; 2,2-hydroxy-1-[4-[4-(trifluoromethyl)phenoxy]phenyl]ethanone.

8. The compound according to claim 1; 2,2-hydroxy-1-[4-[4-(methylthio)phenoxy]phenyl]ethanone.

9. The compound according to claim 1; 2,2-hydroxy-1-[4-[[3-(trifluoromethyl)phenyl]thio]phenyl]ethanone.

10. The compound according to claim 1; α-hydroxy-β-oxo-4-[[3-(trifluoromethyl)phenyl]amino]-benzeneethanesulfonic acid, sodium salt.

11. The compound according to claim 1; 4-[(3-chlorophenyl)amino]-α-hydroxy-β-oxo-benzeneethanesulfonic acid, sodium salt.

12. The compound according to claim 1; α-hydroxy-β-oxo-3-[3-(trifluoromethyl)phenoxy]benzeneethanesulfonic acid, sodium salt.

13. The compound according to claim 1; α-hydroxy-β-oxo-4-[3,5-bis(trifluoromethyl)phenoxy]benzeneethanesulfonic acid, sodium salt.

14. The compound according to claim 1; 2,2-dihydroxy-1-[4-(phenylamino)phenyl]ethanone.

15. The compound according to claim 1; α-hydroxy-β-oxo-4[[4-(trifluoromethyl)phenyl]amino]benzeneethanesulfonic acid, sodium salt.

16. The compound according to claim 1; α-oxo-4-[3-(trifluoromethyl)phenoxy]benzeneethanal, monohydrate.

17. A method of treating diabetes mellitus in a mammal in need of such treatment which comprises administering to said mammal an effective antidiabetic amount of a compound as recited in claim 1.

18. A method of treating hyperglycemia in a mammal in need of such treatment which comprises administering to said mammal an effective hypoglycemic amount of a compound as recited in claim 1.

19. A pharmaceutical antidiabetic composition which comprises an effective antidiabetic amount of a compound as recited in claim 1 in association with a pharmaceutically acceptable carrier.

20. A pharmaceutical hypoglycemic composition which comprises an effective hypoglycemic amount of a compound as recited in claim 1 in association with a pharmaceutically acceptable carrier.

* * * * *